(12) United States Patent
Fenyvesi et al.

US008618184B2

(10) Patent No.: US 8,618,184 B2
(45) Date of Patent: *Dec. 31, 2013

(54) POLYURETHANE FOAMS CONTAINING BRANCHED POLY(TRIMETHYLENE ETHER) POLYOLS

(75) Inventors: Gyorgyi Fenyvesi, Wilmington, DE (US); Raja Hari Poladi, Bear, DE (US); Hari Babu Sunkara, Hockessin, DE (US)

(73) Assignee: E I du Pont de Nemours and Company, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/600,884

(22) Filed: Aug. 31, 2012

(65) Prior Publication Data

US 2012/0322907 A1    Dec. 20, 2012

Related U.S. Application Data

(62) Division of application No. 13/220,030, filed on Aug. 29, 2011.

(60) Provisional application No. 61/415,388, filed on Nov. 19, 2010.

(51) Int. Cl.
*C08G 18/48* (2006.01)
*C08G 18/67* (2006.01)
*C08J 9/04* (2006.01)

(52) U.S. Cl.
USPC ............................... 521/174; 528/76; 528/77

(58) Field of Classification Search
USPC ......................................................... 521/174
See application file for complete search history.

(56) References Cited

U.S. PATENT DOCUMENTS

| 5,981,781 | A | 11/1999 | Knowlton |
| 7,074,968 | B2 | 7/2006 | Sunkara et al. |
| 7,386,267 | B2 | 6/2008 | Abe et al. |
| 7,691,914 | B2 | 4/2010 | Abraham et al. |
| 2006/0004174 | A1 | 1/2006 | Omori et al. |
| 2008/0039582 | A1 | 2/2008 | Sunkara et al. |
| 2008/0194726 | A1 | 8/2008 | Ng et al. |
| 2009/0124719 | A1 | 5/2009 | Creazzo et al. |
| 2009/0280709 | A1 | 11/2009 | Rukavina et al. |

FOREIGN PATENT DOCUMENTS

WO    2010119494 A1    10/2010

OTHER PUBLICATIONS

Polyurethanes, Encyclopedia of Polymer Science and Technology, John Wiley & Sons, Inc. Publisher (2001), vol. 4, pp. 26-72.
Terheiden et al., Scientific Approach to the Question "Why Natural Oil Based Polyols Affect the Physical Properties of Conventional Slabstock Foam", Polyurethane Magazine Internation, Issue 5 (2010) pp. 279-289.
International Search Report, PCT International Application No. PCT/US2011/049536, Mailed Apr. 9, 2012.
Espacenet, Abstract Translation for WO2010/119494A1, (2012).
Terheiden et al., Scientific Approach to the Question "Why Natural Oil Based Polyols Affect the Physical Properites of Conventional Slabstock Foam", Polyurethane Magazine Internation, Issue 5 (2010), pp. 279-289.
International Search Report, PCT International Application No. PCT/US2011/049536, Mailed April 9, 2012.

*Primary Examiner* — Rabon Sergent (57) ABSTRACT

Disclosed is branched poly(trimethylene ether)polyols prepared from the acid catalyzed polycondensation reaction of 1,3-propanediol, and at least one triol comonomer selected from 1,1,1-tris(hydroxymethyl)ethane and 1,1,1-tris(hydroxymethyl)propane. Also disclosed is a branched poly(trimethylene ether)polyol with an equivalent hydroxyl functionality of about 2.1 to about 3.2 and a $M_n$ of about 200 to about 6000. The polyols are useful in the preparation of polyurethane rigid and flexible foams.

6 Claims, 1 Drawing Sheet

POLYURETHANE FOAMS CONTAINING BRANCHED POLY(TRIMETHYLENE ETHER) POLYOLS

This application claims the benefit of U.S. Provisional Application No. 61/415,388, filed Nov. 19, 2010.

FIELD OF THE INVENTION

The present invention relates to polyurethane foams containing branched poly(trimethylene ether)polyols and to compositions comprising the branched poly(trimethylene ether)polyols.

BACKGROUND

Commercially-available polyurethane foams, elastomers and aqueous polyurethane dispersions currently are generally produced using polyether diols, polyols derived from polymerization of ethylene oxide and propylene oxide, polyester polyols, vegetable oil-based polyols, and blends of two or more thereof. The majority of the polyurethanes are prepared from petroleum based feedstocks. While the polyurethane foams prepared using these raw materials exhibit useful properties, they suffer from the fact that the starting materials are petroleum based and not available from renewable sources.

U.S. Pat. No. 6,946,539, US2007/0129524A1, US2009/0124719A1, and US2008/0039582A1, disclose polyurethanes prepared using a poly(trimethylene ether)glycol. Poly(trimethylene ether)glycol (PO3G) is readily prepared by polycondensation of 1,3-propanediol (and optionally other glycols such as ethylene glycol) which, as previously disclosed in U.S. Pat. No. 5,633,362, U.S. Pat. No. 5,686,276 and U.S. Pat. No. 5,821,092, can be prepared by a fermentation process using a renewable biological source. The disclosed renewably sourced PO3G polymers are linear polyether glycols having a number average hydroxyl functionality of about 2 or slightly less than 2 due to the presence of low unsaturated end groups. The lack of high hydroxyl functionality renders the renewable sourced poly(trimethylene ether) glycols of limited use in polyurethane foams.

Natural oil polyols (NOPs) having high hydroxyl functionality have been used to replace petrochemical based polyols in production of polyurethane rigid and flexible foams. However, making flexible polyurethane foams from the NOPs having a renewable content more than about 50%, and less than about 50% petroleum based content, and having desirable performance characteristics can be challenging because of their chemistry and properties relative to conventional polyether polyols. For example, NOPs generally have less-reactive sterically hindered secondary hydroxyl groups, unsaturation, greater hydrophobicity as compared to conventional oils, and can have inconsistencies in composition. Foams made from NOPs can be less flexible and/or less resilient than conventional flexible polyurethane foams.

A renewably sourced polyol having hydroxyl functionality greater than two, with low freezing point and having a good balance between hydrophilic and hydrophobic character would have benefits in production of products such as foams, polyurethane themosets, coatings, adhesives and sealants with excellent properties, as well as many other end uses.

SUMMARY

One aspect of the invention is a branched poly(trimethylene ether)polyol comprising repeating units of Formula I, Formula II, and Formula III

I

II

III wherein R is methyl or ethyl and Q is selected from Formula (IIIa) and (IIIb):

IIIa

IIIb wherein m is 1-20 and n is 1 to 3, and further comprising end groups of Formula IV, V, and VI:

IV

V

VI

Another aspect of the present invention is a composition comprising a blend of a branched poly(trimethylene ether) polyol comprising repeating units of Formula I, Formula II, and Formula III

I

-continued

II

III wherein R is methyl or ethyl and Q is selected from Formula (IIIa) and (IIIb):

IIIa

IIIb wherein m is 1-20 and n is 1 to 3 and further comprising end groups of Formula IV, V, and VI:

IV

V

VI and one or more other polyols selected from petroleum based polyols and vegetable oil based polyols.

Another aspect of the invention is a polyurethane foam comprising the branched poly(trimethylene ether)polyol, optionally blended with one or more other polyols selected from petroleum based polyols and vegetable oil based polyols.

In some embodiments, the branched poly(trimethylene ether)polyol is renewably sourced.

These and other aspects of the invention will be apparent to one skilled in the art in view of the following specification and claims.

DETAILED DESCRIPTION

By "triol" is meant a compound containing three reactive —OH groups. The compound is typically an alkane of 3 to 10 carbons.

By "branched" is meant a polymer molecule that is composed of a main chain with one or more substituent side chains or branches.

By "polyol" is meant a polymer molecule having an equivalent hydroxyl functionality greater than 2.

By "equivalent hydroxyl functionality" is meant the average number of hydroxyl groups per molecule of a polyol.

By "amorphous polyol" is meant a polyol that possess little or no degree of crystallinity and a melt enthalpy less than 10 J/g as determined in a second heat differential scanning calorimetry (DSC) spectrum.

By "semicrystalline polyol" is meant a polyol that has distinct cold crystallization ($T_a$), melt temperature ($T_m$) peaks, and a melt enthalpy ($\Delta H_m$) greater than 10 J/g as determined by a second heat differential scanning calorimetry (DSC) spectrum.

By "high oleic vegetable oil based polyol" is meant a polyol derived from vegetable oil comprising triglycerides of fatty acids of which more than 65 weight percent are oleic acid.

By "polyisocyanate" is meant a polyisocyanate or polyisocyanurate having 2 or more than isocyanate groups.

By "polyurethane foam" is meant a rigid, flexible, or semi flexible foam. The flexible foam can be slabstock or molded foam.

Disclosed herein is a branched poly(trimethylene ether) polyol comprising repeating units of Formula I, Formula II, and Formula III:

I

II

III wherein R is methyl or ethyl and Q is selected from Formula (IIIa) and (IIIb):

IIIa wherein m is 1-20 and n is 1 to 3. The polyol further comprises end groups of Formula IV, V, and VI:

In some embodiments, Q of both Formula (IIIa) and Formula (IIIb) are present.

The branched poly(trimethylene ether)polyols are suitable for use in polyurethane foams.

In some embodiments, the poly(trimethylene ether)polyols are renewably sourced, and in further embodiments they can be used in blend compositions with natural oil based polyols. Renewably sourced branched poly(trimethylene ether)polyols, optionally blended with vegetable oil based polyols, can be used as an alternative to petroleum based polyols in polyurethane foams.

In some preferred embodiments, the branched poly(trimethylene ether)polyol is amorphous.

The branched poly(trimethylene ether)polyols preferably have a $M_n$ of about 200 to about 6000.

The branched poly(trimethylene ether)polyols disclosed herein can comprise primary hydroxyl groups present both as pendant $CH_2OH$ groups and chain end $CH_2OH$ groups and do not contain secondary hydroxyl groups. The primary hydroxyl groups are located randomly on main and branched chains of a molecule as well as at the chain ends. The absence of secondary hydroxyl end groups and steric hindered hydroxyl groups on the main polymeric chain or a side chain makes these poly(trimethylene ether)polyols more reactive towards polyisocyanates, carboxylic acids and their esters than many conventional polyols containing secondary hydroxyl groups.

The branched poly(trimethylene ether)polyols can be made from the polycondensation reaction of 1,3-propanediol and at least one triol comonomer selected from 1,1,1-tris(hydroxymethyl)ethane and 1,1,1-tris(hydroxymethyl)propane. The 1,3-propanediol can be 1,3-propanediol alone or dimer or trimer of 1,3-propanediol, and mixtures thereof.

In one embodiment, the triol comonomer is 1,1,1-tris(hydroxymethyl)ethane and in another embodiment the triol comonomer is 1,1,1-tris(hydroxymethyl)propane.

When a triol comonomer is incorporated into the polymer during the polycondensation process, the resulting branched poly(trimethylene ether)polyol is a random polymer having at least one branch in a molecule, as characterized by proton NMR. As the amount of the triol comonomer in the polymer increases the degree of branching increases, and higher amounts of comonomer can lead to crosslinked polyol which is undesirable.

In one embodiment, the branched poly(trimethylene ether) polyol comprises from about 90 to about 99 mole % 1,3-propanediol and from about 1 to about 10 mole % triol comonomer. In one embodiment the branched poly(trimethylene ether)polyol comprises from about 2 to about 8 mole % triol comonomer.

In another embodiment, the branched poly(trimethylene ether)polyol comprises from about 90 to about 99 mole % 1,3-propanediol and from about 1 to about 10 mole % 1,1,1-tris(hydroxymethyl)ethane comonomer. In another embodiment the branched poly(trimethylene ether)polyol comprises from about 90 to about 99 mole % 1,3-propanediol and from about 1 to about 10 mole % 1,1,1-tris(hydroxymethyl)propane comonomer.

In one embodiment, the branched poly(trimethylene ether) polyol comprises about 90 to about 99 mole % repeating units of Formula I and about 1 to about 10 mole % repeating units of one or both of Formula II and Formula III. In one embodiment the branched poly(trimethylene ether)polyol comprises about 2 to about 8 mole % repeating units of one or both of Formula II and Formula III.

When the repeating units of one or both of Formula II and Formula III where R is methyl are present at higher than about 2.5 mole percent the branched poly(trimethylene ether) polyol is an amorphous liquid polymer. In some embodiments, the repeating units of Formula II and/or Formula III are present in amounts of about 2.8 mole percent or higher, or about 3.2 mole percent or higher, The degree of the crystallinity of the poly(trimethylene ether)polyols disclosed herein depends on several factors that include type and amount of comonomer in the backbone, number of branches, and the length of branched and main chains. Linear poly(trimethylene ether)glycol homopolymers prepared from polycondensation of 1,3-propanediol are semicrystalline polymers having a distinct cold crystallization temperature ($T_c$) peak at about −37° C., melt temperature ($T_m$) peaks in the range of 5-20° C. depending on the molecular weight, and a enthalpy of melting ($\Delta H_m$) of about 80-95 J/g.

In contrast to linear poly(trimethylene ether)glycol homopolymers, the poly(trimethylene ether)polyols disclosed herein are preferably amorphous in nature. The poly (trimethylene ether)polyol does not exhibit a $T_c$ or $T_m$ when the triol comonomer, 1,1,1-tris(hydroxymethyl)ethane, is incorporated into the backbone at about 2.8 mol % and higher.

The functionality and functionality distribution are useful parameters to characterize the composition of polyols. The branched poly(trimethylene ether)polyol prepared from polycondensation is a mixture of molecules having from about 2 to about 5 hydroxyl groups per molecule, and the number of hydroxyl groups in a polyol molecule depends upon the type and amount of comonomer and manufacturing polycondensation process. The physical properties therefore can be controlled by varying the composition.

One practical method for functionality determination is based on the assessment of the number average molecular weight ($M_n$) of the branched poly(trimethylene ether)polyol by gel permeation chromatography together with hydroxyl number determination from titration. The hydroxyl functionality (f) is calculated by using the equation:

$$f = M_n \times OH\#/56100$$

where $M_n$ is the number average molecular weight and OH# is the total hydroxyl number determined by titration, 56100 is a constant related to KOH.

Alternatively, the equivalent hydroxyl functionality, fe, of the mixture can be calculated using the following equation:

$$fe = \frac{\text{Total number of hydroxyl groups}}{\text{Total number of molecules}}$$

The branched poly(trimethylene ether)polyols disclosed herein typically have hydroxyl numbers in the range of 550 to 65 mg KOH/g, the equivalent hydroxyl functionality ranging from about 2.1 to about 3.2 and the number average molecular weight ($M_n$) is from about 200 to about 6000, or from about 250 to about 5000, or from about 1000 to about 2500.

Typically the branched poly(trimethylene ether)polyols disclosed herein have a polydispersity index or molecular weight distribution (MWD) within the range of 1.5 to 2.8. The polyol may have residual unreacted diol and triol monomers and are part of the MWD.

The branched poly(trimethylene ether)polyols disclosed herein have viscosities in the range from about 50 to 5000 cPs at 40° C. In general, the viscosity of the branched poly(trimethylene ether)polyol increases with increase in molecular weight and also with increase in hydroxyl functionality.

The branched poly(trimethylene ether)polyols have typically an APHA color of less than 300, more typically less than 200, and most typically less than 100. The color of the polyols can be further improved, if desired, by the addition of a color-reducing aid such as activated carbon black. One suitable method is disclosed in U.S. Patent Application No. 2004/022516, filed Aug. 5, 2003.

The surface tension of the branched poly(trimethylene ether)polyols disclosed herein is about 40 to about 42 dynes/cm. The surface tension is a measure of the inward force acting on the surface of a liquid due to the attraction of molecules in the liquid. In general, high levels of intermolecular forces among the molecules in a liquid have high values of surface tension.

The more hydroxyl functional groups in the molecule of the branched poly(trimethylene ether)polyol in general, the higher the hydrophilicity of the polyol and thereby the greater the degree of intermolecular interactions and viscosity; however the presence of methyl or ethyl pendent groups in the molecule can decrease its hydrophilicity. The measured surface tensions of the branched poly(trimethylene ether)polyols are very close to that of homopolymers of linear poly(trimethylene ether)glycol, which indicates that the hydrophilicity of the poly(trimethylene ether)polyol is similar to that of the homopolymers in spite of higher hydroxyl functionality.

The branched copolyether poly(trimethylene ether)polyols disclosed herein also have relatively few unsaturation (allyl) end groups, typically less than 30 meq/kg, more typically less than 25 meq/kg. Unsaturation end groups in polyol can act as chain terminating agents in polyurethane chemistry and can limit the molecular weight of the polyurethane and thereby affect the physical properties. In contrast to poly(trimethylene ether)glycol homopolymers with hydroxyl functionality of less than 2, the impact of low unsaturation end groups in the branched poly(trimethylene ether)polyol on properties of polyurethane is less significant because the average hydroxyl functionality is greater than 2.

The conventional additives commonly used in polyether polyols can be added to the branched poly(trimethylene ether)polyols. Such additives include delusterants (e.g., $TiO_2$, zinc sulfide or zinc oxide), colorants (e.g., dyes), stabilizers (e.g., antioxidants, ultraviolet light stabilizers, heat stabilizers) fillers, flame retardants, pigments, antimicrobial agents, antistatic agents, optical brighteners, extenders, processing aids, viscosity boosters, and other functional additives. As a specific example, an antioxidant prevents oxidation of polyethers that are subject to oxidation during storage. Preferred antioxidant stabilizers are butylated hydroxy toluene (BHT) and Vitamin E, used in a quantity of about 50 to about 5000 micrograms/g based on the weight of the polymer. Preferably, the amount of antioxidant is from about 100 to about 200 micrograms/g.

The process of making the branched poly(trimethylene ether)polyols disclosed herein can be a batch, semi-continuous, or continuous. The triol comonomer can be added prior to or during initial polymerization of 1,3-propanediol. Suitable processes include those disclosed in U.S. Pat. Nos. 6,720,459 and 6,977,291, with further reaction of desired comonomer with the 1,3-propanediol reactant.

The 1,3-propanediol can be obtained by any of the various well known chemical routes or by biochemical transformation routes. In some preferred embodiments, the 1,3-propanediol is obtained biochemically from a renewable source ("biologically-derived" 1,3-propanediol).

A particularly preferred source of 1,3-propanediol is via a fermentation process using a renewable biological source. As an illustrative example of a starting material from a renewable source, biochemical routes to 1,3-propanediol have been disclosed that utilize feedstocks produced from biological and renewable resources such as corn feed stock. For example, bacterial strains able to convert glycerol into 1,3-propanediol are found in the species *Klebsiella, Citrobacter, Clostridium*, and *Lactobacillus*. The technique is disclosed in several patents, including U.S. Pat. No. 5,633,362, U.S. Pat. No. 5,686,276 and U.S. Pat. No. 5,821,092. For example, U.S. Pat. No. 5,821,092 discloses, inter alia, a process for the biological production of 1,3-propanediol from glycerol using recombinant organisms. The process incorporates *E. coli* bacteria, transformed with a heterologous pdu diol dehydratase gene, having specificity for 1,2-propanediol. The transformed *E. coli* is grown in the presence of glycerol as a carbon source and 1,3-propanediol is isolated from the growth media. Since both bacteria and yeasts can convert glucose (e.g., corn sugar) or other carbohydrates to glycerol, the processes disclosed in these publications provide a rapid, inexpensive and environmentally responsible source of 1,3-propanediol monomer.

The biologically-derived 1,3-propanediol, such as produced by the processes disclosed and referenced above, contains carbon from the atmospheric carbon dioxide incorporated by plants, which compose the feedstock for the production of the 1,3-propanediol. In this way, the biologically-derived 1,3-propanediol contains only renewable carbon, and not fossil fuel-based or petroleum-based carbon. The branched poly(trimethylene ether)polyols made from the biologically-derived 1,3-propanediol, therefore, may have less impact on the environment as the 1,3-propanediol used in the compositions does not deplete diminishing fossil fuels and, upon degradation, releases carbon back to the atmosphere for use by plants once again. Thus, the compositions disclosed herein can be characterized as more natural and having less environmental impact than similar compositions comprising petroleum based polyols.

Biologically-derived 1,3-propanediol, and compositions comprising biologically-derived 1,3-propanediol, therefore, may be distinguished from their petrochemical derived counterparts on the basis of $^{14}C$ ($f_M$) and dual carbon-isotopic fingerprinting, indicating new compositions of matter. The ability to distinguish these products is beneficial in tracking these materials in commerce. For example, products comprising both "new" and "old" carbon isotope profiles may be distinguished from products made only of "old" materials. Hence, the instant materials may be followed in commerce on the basis of their unique profile and for the purposes of defining competition, for determining shelf life, and especially for assessing environmental impact.

Preferably the 1,3-propanediol used as the reactant or as a component of the reactant will have a purity of greater than about 99%, and more preferably greater than about 99.9%, by weight as determined by gas chromatographic analysis. Particularly preferred are the purified 1,3-propanediols as disclosed in US20040260125A1, US20040225161A1 and US20050069997A1, and poly(trimethylene ether)glycol made therefrom as disclosed in U.S. Pat. No. 7,323,539.

The renewable sourced carbon content of the branched poly(trimethylene ether)polyol is greater than 70%, typically greater than 80% and more typically greater than 90% by weight of the total carbon content. The bio based carbon content is either calculated based on number of carbons or determined according to ASTM-D6866.

The renewably sourced branched poly(trimethylene ether) polyols can be used to replace completely or partially one or more petroleum based polyols that are being used to make end products such as polyurethane foams and elastomers. The renewably sourced branched poly(trimethylene ether)polyols can also be blended with petroleum-based polyols and/or natural oil based polyols. "Natural oils" is used herein to refer to non-petroleum based, naturally occurring oils.

The branched poly(trimethylene ether)polyols can blended with one or more polyols derived from natural oils, such as, for example example, the polyols derived from natural oils including vegetable oil based polyols selected from soybean oil, palm based oils, sunflower oil, safflower oil, corn oil, canola oil, sesame oil, linseed oil, olive oil, cottonseed oil, castor oil and combinations thereof. Renewably sourced poly(trimethylene ether)polyols may be preferred for such blends. The vegetable oils can be natural or genetically modified vegetable oils, for example, high oleic soybean oil, high oleic sunflower oil, high oleic safflower oil, high oleic peanut oil. "High oleic" is used in the art to refer to oils having 65% or more oleic content. Other than castor oil, which has hydroxyl groups, all other vegetable oils need to be converted into polyols by chemical modifications. Although there are several known methods in the literature to make polyols from vegetable oils, a typical method comprises two steps: (i) partial or complete epoxidation of oils with peroxyacid that converts a portion or all of the double bonds of the oil to epoxide groups, (ii) ring opening with an alcohol in the presence of a catalyst that converts a portion or all of the epoxide groups into hydroxyl groups. U.S. Pat. No. 7,691,914 discloses one method of making polyols from vegetable oils.

The polyols derived from genetically modified high oleic vegetable oil are preferred over natural oil based polyols with low levels of oleic acid. In particular, genetically modified high oleic soybean oil is more homogenous in composition than commodity soybean oil, due to its relatively high concentrations of monounsaturated oleic acid (greater than 65%) and relatively low levels of polyunsaturated linoleic and linolenic acids (less than 20%). In addition to the mono and polyunsaturated fatty acids, the vegetable oils can contain saturated fatty acids. The amount of unsaturation in vegetable oils can be quantified by iodine value and typically the iodine values for the vegetable oils will range from about 40 to 240. For example, commodity soybean oil has an iodine value of about 120-140 which corresponds to 4.6 double bonds per molecule, whereas genetically modified soybean oil has an iodine value less than 90. U.S. Pat. No. 5,981,781 discloses a process of making high oleic soybean oil.

A preferred polyol blend comprises a branched poly(trimethylene ether)polyol and a polyol derived from genetically modified high oleic soybean oil. The amount of branched poly(trimethylene ether)polyol in the blend can range from about 1 to about 99% by weight of the total weight of the blend. In some embodiments, the amount of branched polyol is from about 10 to about 90% by weight of the total weight of the blend, or about 20 to about 80% by weight of the total weight of the blend.

The branched poly(trimethylene ether)polyols or the branched poly(trimethylene ether)polyol blends with polyols derived from vegetable oils disclosed herein have a wide variety of end use applications. One application is in the manufacture of polyurethanes for CASE (coatings, adhesives, sealant and elastomer) and foam applications. For rigid polyurethane foam applications, short chain polyols with high hydroxyl number and high functionality are preferred. For flexible slabstock or molded polyurethane foam applications, long chain polyols with lower hydroxyl number and functionality are preferred. The production and applications of polyurethanes are well known in the art. See Ulrich, H. 2001, Polyurethanes, Encyclopedia of Polymer Science and Technology, John Wiley & Sons, Inc.

The expression "polyurethane foam" as used herein refers to closed cellular or open cellular products as obtained by reacting di- or polyisocyanates with isocyanate-reactive hydrogen containing compounds such as polyols, aminoalcohols and/or polyamines, using blowing agents, such as fluorocarbons, fluoroolefins, hydrocarbons, chlorocarbons, acetone, methyl formate, and $CO_2$ generated in situ by reaction of the polyisocyanate with water added to the formulation.

The slabstock or molded polyurethane foams comprise the reaction product of ingredients comprising: (a) an isocyanate-reactive compound comprising a branched poly(trimethylene ether)polyol having equivalent hydroxyl functionality from about 2.4 to about 3.2 or an isocyanate-reactive compound comprising a polyol blend of from about 1 to about 99% by weight of the branched poly(trimethylene ether)polyol and from about 99 to about 1% by weight of vegetable oil based polyol; (b) a polyisocyanate component comprising a di or polyisocyanate and (c) a blowing agent. In some preferred embodiments, the vegetable oil based polyol is the high oleic soybean oil based polyol.

The branched poly(trimethylene ether)polyols disclosed herein have many useful properties when used alone or blended with other polyols in making polyurethane foams. The useful properties of the polyol include high hydroxyl functionality, reactive primary hydroxyl groups, low glass transition temperature, low freezing point (liquid with no or little degree of crystallinity), low viscosity, good hydrophilic and hydrophobic balance, high renewable content, no odor, low acid number and low color. They offer flexibility, resilience and hydrolytic stability to the foams.

EXAMPLES

Characterization

Using the NMR method, the number average molecular weight and the number average functionality of the branched poly(trimethylene ether)poly(trimethylene ether)polyol were calculated.

¹H NMR spectrum (CDCl₃ and trifluoroacetic anhydride solvents) of the copolymer had the following main chemical shifts: δ=0.94, 1.00, 1.008 (s, CH₃—C(CH₂O)₃), 1.89, 1.93, 2.01 (t, —O—CH₂—CH₂—CH₂—O, backbone), 3.30 to 3.58 (t, CH₂—O—CH₂— backbone), 4.3-4.4 (t, HO—CH₂—C(CH₃)), 4.46 (HO—CH₂)

Proton NMR distinguishes the protons corresponding to the end groups (CH₂—OH), middle ether groups (CH₂—O—CH₂), methyl groups of co-monomer with varying functionality (CH₃—C(CH₂O)₃). As the branched 1,1,1-tris(hydroxymethyl)ethane with three reacted hydroxyls do not have end groups, methyl groups of 1,1,1 tris(hydroxymethyl) ethane were used for calculating molecular weight and functionality contribution from 1,1,1-tris(hydroxymethyl)ethane. Methyl group carbons have three hydrogens and the carbon atoms of end groups and ether linkages have two hydrogens. Hence, the response area of methyl groups needs to be multiplied with ⅔ to equalize.

The number average molecular weight ($M_n$) of the branched poly(trimethylene ether)polyol was calculated using the following equation:

$$M_n = (DP * \text{mole \%} PDO * 58)/100 +$$
$$(DP * \text{mole \%} TME * 102)/100 + 18 - \text{unsat ends/mole} * 18$$

$$DP = \frac{\text{Total number of ether linkages} + \text{unsaturated end groups}}{PDO \text{ ends} + \text{unsaturated ends} + TME \text{ ends} - \text{branched } TME} + 1$$

$$DP = \frac{e+u}{h+u+m-t} + 1$$

and the equivalent hydroxyl functionality, or functionality, was calculated as shown below, using the following abbreviations:
DP Degree of polymerization
TME 1,1,1 Tris(hydroxymethyl)ethane
u Unsaturated ends per polymer molecule
e Area of total ether linkages
h Area of PDO end groups
m, d, t ⅔ of the areas of 1,1,1-tris(hydroxymethyl)ethane methyl groups with mono, di and tri ether linkages, respectively.

$$\text{Functionality} = \frac{\text{Total number hydroxyl end groups}}{\text{Total number of molecules}}$$

$$\text{Functionality} = \frac{2m+d+h}{(e+h+u+m-t)/2DP}$$

Polydispersity Index ($M_w/M_n$) of the polyols was measured by gel permeation chromatography (GPC). The GPC instrument was calibrated using linear poly(trimethylene ether)glycol homopolymer. ASTM method D445-83 and ASTM method D792-91 were used to determine the absolute (dynamic) viscosity and density of the polymer, respectively. The color of polyols was measured using Hunter Lab Color Quest colorimeter and expressed as APHA index. The phase transitions such as melting, crystallization and glass transition temperatures of the polyols were obtained from differential scanning calorimetry (DSC). Surface tension was measured for the polyols by ring (DuNouy) method using Cahn dynamic contact angle analyzer (model DCA-312).

Example 1

450 g (5.9 moles) of 1,3 propanediol (Susterrai® propanediol from DuPont Tate & Lyle Bioproducts, Loudon, Tenn.), 78.9 g (0.66 moles; 10 mol %) of 1,1,1-tris(hydroxymethyl)ethane (Aldrich) and 5.34 g of $H_2SO_4$ (VWR, 95 wt %) charged into a 1 L four-neck round bottomed flask fitted with mechanical stirrer and condenser to cool and collect byproducts. The reactor was flushed with dry nitrogen gas to remove air. The reaction mixture was heated to 165° C. and reaction was continued for 5.5 h. The reaction was stopped and the reaction products were allowed to cool.

The obtained product was mixed with 500 mL of water and hydrolyzed at 90° C. for 2 h. The temperature was then reduced to 60° C. 500 mL of 2 wt % $Na_2CO_3$ solution was slowly added and mixed for 30 min. The product was transferred into separating funnel. After separation the lower part was collected and mixed with 1 L of water and again transferred into separation funnel. The lower organic part was collected and dried at 90° C. using rotary evaporator. The obtained product was characterized using NMR, GPC, DSC and wet chemical analysis. (titration and viscosity measurement). The color of the branched polyol was low and found to be 53 APHA.

Comparative Example 1

319 g (4.19 moles) of Bio-PDO™, 96.28 g (1.04 moles) of glycerol (Aldrich) and 3.75 g of $H_2SO_4$ (VWR, 95 wt %) was charged into 1 L four-neck round bottomed flask fitted with mechanical stirrer and condenser to cool and collect byproducts. The reactor was flushed with dry nitrogen gas to remove air. The reaction mixture was heated to 166° C. and reaction was continued for 5.5 h. The heating was then stopped and the reaction mixture was allowed to cool. The obtained product was purified as described in Example 1.

The resulting product was dark in color which is undesirable for many applications.

Example 2

2700 g (35.48 moles) of 1,3-propanediol, 270 g (2.25 moles; 6 mol %) of 1,1,1-tris(hydroxymethyl)ethane (Aldrich) and 30.1 g of $H_2SO_4$ (VWR, 95 wt %) charged into 5 L four-neck round bottomed flask fitted with mechanical stirrer and condenser to cool and collect byproducts. The reactor was flushed with dry nitrogen gas to remove air. The reaction mixture was heated to 166° C. and reaction was continued for 14 h. The heating was then stopped and the reaction product was allowed to cool.

The obtained product was neutralized with 68 g sodium carbonate solution (68 g in 120 mL of deionized water) at 120° C. for 6 h. The product was filtered using solka-floc filter aid. The product was characterized as disclosed in Example 1.

Example 3

2733 g (35.9 moles) of 1,3-propanediol, 120 g (1 mole; 2.7 mol %) of 1,1,1-tris(hydroxymethyl)ethane (Aldrich), 25.87 g of $H_2SO_4$ (VWR, 95 wt %) and 2.54 g of sodium carbonate dissolved in 10.5 mL water was added charged into 5 L four-neck round bottomed flask fitted with mechanical stirrer and condenser to cool and collect byproducts. The reactor was flushed with dry nitrogen gas to remove air. The reaction mixture was heated to 166° C. and reaction was continued for 21 h 15 min. The heating was then stopped and the reaction product was allowed to Cool.

The obtained product was mixed with 1.5 L of water and hydrolyzed at 95° C. for 4 h. Then 330 mL of 10 wt % $Na_2CO_3$ solution was slowly added and mixed for 30 min. The product was distilled under reduced pressure to remove water and filtered using solka-floc filter aid. The product was characterized using $^1$H NMR.

Example 4

2433 g (32 moles) of 1,3-propanediol, 120 g (1 mole; 3 mol %) of 1,1,1-tris(hydroxymethyl)ethane (Aldrich), 25.37 g of $H_2SO_4$ (VWR, 95 wt %) and 2.54 g of sodium carbonate dissolved in 10.5 mL water was added charged into 5 L four-neck round bottomed flask fitted with mechanical stirrer and condenser to cool and collect byproducts. The reactor was flushed with dry nitrogen gas to remove air. The reaction mixture was heated to 166° C. and reaction was continued for 21 h 45 min. The heating was then stopped and the reaction product was allowed to cool.

The obtained product was mixed with 1.5 L of water and hydrolyzed at 95° C. for 4 h. Then 330 mL of 10 wt % $Na_2CO_3$ solution was slowly added and mixed for 30 min. The product was distilled under reduced pressure to remove water and filtered using solka-floc filter aid. The product was characterized using $^1$H NMR. The color of the polyol was found to be 150 APHA

Example 5

The procedure was similar to the procedure disclosed in Example 4 except the sulfuric acid amount was 25.9 g and the reaction time was 22 hours. The color of the polyol was found to be 162 APHA Table 1 below summarizes the composition and properties of the branched poly(trimethylene ether)polyols prepared in Examples 1-5 using proton NMR method.

TABLE 1

| Ex | $M_n$ | OH # | Average Functionality | PDO mole % | $MeC(CH_2OH)_3$ mole % |
|----|------|------|----------------------|------------|-----------------------|
| 1 | 244 | 522 | 2.3 | 92.5 | 7.5 |
| 2 | 982 | 157 | 2.8 | 94.8 | 5.2 |
| 3 | 1358 | 104 | 2.6 | 97.5 | 2.5 |
| 4 | 2137 | 76.5 | 2.9 | 97.2 | 2.8 |
| 5 | 2171 | 75.5 | 2.9 | 97.2 | 2.8 |

As shown in Table 1, it is possible to synthesize wide range of branched poly(trimethylene ether)polyols having different hydroxyl numbers, functionality and molecular weights by selecting the right amount of the triol comonomer and the process conditions. The branched poly(trimethylene ether) polyol of example 1 is particularly suitable for polyurethane rigid foam applications because this poly(trimethylene ether) polyol comprised of short chains with high hydroxyl numbers of at least 250 whereas the rest of the poly(trimethylene ether)polyols are more suitable for flexible foam applications.

Table 2 below compares the properties of the branched poly(trimethylene ether)polyols with linear homopolymers. The Comparative Examples were commercial Cerenol® homopolymers obtained from E. I. du Pont de Nemours and Company, Wilmington, Del.

TABLE 2

| Property | Units | Comp. Ex 2 | Comp Ex 3 | Comp. Ex 4 | Example 2 | Example 3 | Example 4 |
|---|---|---|---|---|---|---|---|
| Bio based carbon content | % | 100 | 100 | 100 | 91.7 | 95.6 | 95.2 |
| Mole percent of triol in polymer | % | 0 | 0 | 0 | 5.2 | 2.5 | 2.8 |
| Hydroxyl number (titration) | mg KOH/g | 107 | 79 | 55 | 157 | 104 | 76 |
| Average Functionality | | 1.98 | 1.98 | 1.97 | 2.82 | 2.59 | 2.9 |
| $M_n$ (GPC) | daltons | 1094 | 1428 | 1971 | 1089 | 1497 | 2091 |
| Polydispersity index | $M_w/M_n$ | 1.63 | 1.73 | 1.79 | 1.85 | 1.92 | 2.20 |
| Unsaturation (NMR) | meq/kg | 14 | 16 | 16 | 20 | 21 | 20 |
| Viscosity | cP | | | | | | |
| @ 40° C. | | 247 | 410 | 839 | 383 | 527 | 1520 |
| @ 100° C. | | 36.2 | 60 | 124 | 45.5 | 73 | 196 |
| Viscosity Index | | 204 | 225 | 262 | 183 | 220 | 264 |
| Density @ 40° C. | g/cc | 1.025 | 1.016 | 1.015 | 1.028 | 1.021 | 1.035 |
| Glass transition temperature ($T_g$) | ° C. | −77 | −77 | −76 | −76 | −76 | −73 |
| Cold crystallization temperature ($T_c$) | ° C. | −37 | −38 | −38 | none | −9 | none |
| Melting temp. ($T_m$) | , ° C. | 8.0; 15.3 | 10.8; 16.1 | 14.4; 17.2 | none | 4.2; 11.5 | none |
| Melting enthalpy | J/g | 83 | 84 | 93 | none | 13 | none |
| Refractive index | | 1.4622 | 1.4625 | 1.4626 | 1.4639 | 1.4648 | 1.4650 |
| Surface tension, | Dynes/cm | 40.1 | 40.8 | 40.0 | 41.2 | 40.5 | 40.7 |

The data in Table 2 demonstrates that about 2.8 mol % of triol or higher incorporation changed the crystalline polymer to amorphous polymer. At above 2.5 mol % of triol incorporation, the degree of crystallization and the rate of crystallization of the poly(trimethylene ether)polyol decreased dramatically, as evident from significantly lower melt enthalpy and higher cold crystallization temperature than the corresponding homopolymer. The molecular weight distribution is slightly broader and viscosity is higher for higher molecular weight branched polyols than that of linear polyol. The surface tension of branched poly(trimethylene ether)polyols are very similar to that of linear polyols suggesting the branched polyols have similar hydrophilic character of linear polyols in spite of higher hydroxyl functionality.

Example 6

2433 g (32 moles) of 1,3-propanediol, 138.5 g (1.15 mole; 3.47 mol %) of 1,1,1-tris(hydroxymethyl)ethane (Aldrich), 25.8 g of $H_2SO_4$ (VWR, 95 wt %) and 2.7 g of sodium carbonate dissolved in 10.5 mL water was added into 5 L four-neck round bottomed flask fitted with a mechanical stirrer and condenser to cool and collect byproducts. The reactor was flushed with dry nitrogen gas to remove air. The reaction mixture was heated to 166° C. and reaction was continued for 21 h 45 min. The heating was then stopped and the reaction product was allowed to cool.

The obtained product was mixed with 1.5 L of water and hydrolyzed at 95° C. for 4 h. Then 150 mL of 21.6 wt % $Na_2CO_3$ solution was slowly added and mixed for 30 min. The product was distilled under reduced pressure to remove water and filtered using solka-floc filter aid. The product was characterized using $^1H$ NMR, and the results are shown in Table 3 below.

TABLE 3

| Ex | $M_n$ | Average Functionality | PDO mole % | MeC(CH$_2$OH)$_3$ mole % |
|---|---|---|---|---|
| 6 | 1544 | 2.8 | 96.85 | 3.15 |

The melting temperature and melting enthalpy of the product from DSC analysis were found to be 10.5° C. and 0.56 J/g respectively. The very low melting enthalpy value indicates that the product is largely amorphous in nature.

Figure 1:
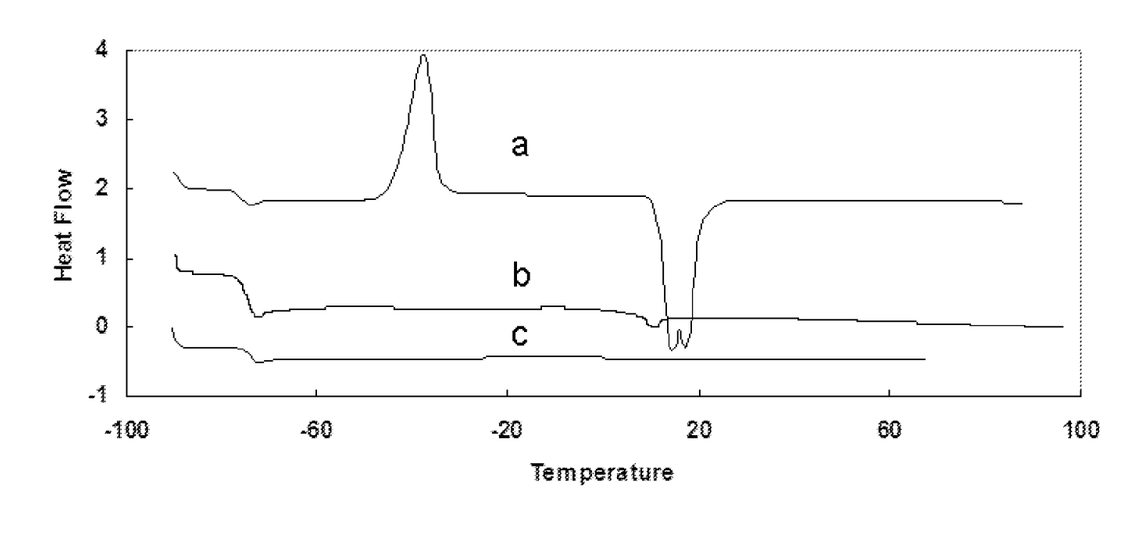
FIG. 1 illustrates a comparison of the phase transitions ($T_g$, $T_c$, and $T_m$) from differential scanning calorimetry spectrum of the branched poly(trimethylene ether)polyols from Examples 4 (b) and 6 (c) with the phase transitions of Cerenol® H-2000 homopolymer (a).

FIG. 1 is the DSC spectra that compares the phase transitions of branched poly(trimethylene ether)polyols from Example 4 (b) and Example 6 (c) vs linear Cerenol® H-2000 homopolymer (a).

Example 7

2436 g (32 moles) of 1,3-propanediol, 134.2 g (1 mole; 3 mol %) of 1,1,1-tris(hydroxymethyl)propane (Aldrich), 25.78 g of $H_2SO_4$ (VWR, 95 wt %) and 2.64 g of sodium carbonate dissolved in 15 mL water was added into 5 L four-neck round bottomed flask fitted with mechanical stirrer and condenser to cool and collect byproducts. The reactor was flushed with dry nitrogen gas to remove air. The reaction mixture was heated to 167° C. and reaction was continued for 21 h 45 min. The heating was then stopped and the reaction product was allowed to cool.

The obtained product was mixed with 1.5 L of water and hydrolyzed at 95° C. for 4 h. Then 330 mL of 10 wt % $Na_2CO_3$ solution was slowly added and mixed for 30 min. The product was distilled under reduced pressure to remove water and was filtered using solka-floc filter aid. The number average molecular weight of the polyol was found to be 2318.

Example 8

A 50/50 blend was prepared my mixing the branched poly(trimethylene ether)polyol (from Example 4) having $M_n$ and a surface tension of 40.7 dynes/cm with a naturally occurring polyol such as castor oil polyol (from Spectrum) having $M_n$ of 980 daltons and a surface tension of 36.0 dynes/cm. The resulting blend was homogeneous (completely miscible) and had a surface tension of 37.4 dynes/cm.

A 50/50 polyol blend by weight was prepared my mixing the branched poly(trimethylene ether)polyol (from Example 4) having very low unsaturation (20 meq/kg) with a renewably sourced vegetable oil based polyol (Agrol® from Bio-Based Technologies®, LLC, Fayetteville, Ark.) having a hydroxyl functionality of 3.6 and high unsaturation (iodine value of about 92 cgI2/g). The resulting blend was homogeneous (completely miscible) indicating excellent compatibility of poly(trimethylene ether)polyol with the vegetable oil based polyol and contain reduced levels of unsaturation and ester groups that provides better oxidative stability and hydrolytic stability than Agrol® polyol.

Flexible Slabstock Polyurethane Foams

Example 9

The foam formulation is prepared by using the ingredients listed in Table 4 Toluene diisocyanate is added to the mixture containing the polyol blend (90/10% by weight of high oleic soybean oil polyol and branched poly(trimethylene ether)polyol), water, catalyst and surfactant, and mixed for less than 10 seconds. The mixture is poured into a cup and is allowed to free rise. The foam is cured in an oven for 15 minutes at 100° C.

Example 10

The foam is prepared as described in Example 9 except the polyol blend is a mixture of 10/90% by weight of high oleic soybean oil polyol and branched poly(trimethylene ether) polyol.

TABLE 4

| Component | Example 9 Parts by weight | Example 10 Parts by weight |
|---|---|---|
| High Oleic Soybean Oil Polyol | 90 | 10 |
| Branched Polyol from Example 4 | 10 | 90 |
| Water | 4 | 4 |
| Silicon type surfactant | 1 | 1 |
| Potassium catalyst | 2 | 2 |
| Amine based catalyst | 0.1 | 0.1 |
| TDI index | 105 | 105 |

The amount of TDI required is calculated based on the total hydroxyl numbers of polyols and water, and the Index of 105.

What is claimed is:

1. A polyurethane foam comprising a branched amorphous poly(trimethylene ether)polyol comprising repeating units of Formula I, Formula II, and Formula III wherein R is methyl and Q is selected from Formula (IIIa) and (IIIb):

wherein m is 1-20 and n is 1 to 3, and further comprising end groups of Formula IV, V, and VI:

wherein the branched poly(trimethylene ether)polyol comprises the repeating units of Formula II and Formula III, together, at from about 2.8 mole percent to about 10 mole percent based on the branched poly(trimethylene ether)polyol, and wherein the branched poly(trimethylene ether)polyol is amorphous.

2. The polyurethane foam of claim 1 wherein the foam is flexible slabstock foam.

3. The polyurethane foam of claim 1 wherein the foam is rigid foam.

4. The polyurethane foam of claim 1 wherein the branched amorphous poly(trimethylene ether)polyol has Mn of about 200 to about 6000.

5. The polyurethane foam of claim 1 wherein the branched amorphous poly(trimethylene ether)polyol has Mn of about 250 to about 5000.

6. The polyurethane foam of claim 1 wherein the branched amorphous poly(trimethylene ether)polyol has an equivalent hydroxyl functionality of about 2.1 to about 3.2.

* * * * *